United States Patent [19]

Winneti et al.

[11] Patent Number: 4,758,324
[45] Date of Patent: Jul. 19, 1988

[54] APPARATUS FOR DETERMINING POTENTIAL DIFFERENCES

[75] Inventors: Michael A. Winneti, Berkshire; Edward Daley, Nelson, both of England

[73] Assignee: Colebrand Limited, London, England

[21] Appl. No.: 783,984

[22] Filed: Oct. 3, 1985

[51] Int. Cl.$^4$ ............................................. G01N 27/46
[52] U.S. Cl. .................................. 204/404; 204/1 T; 204/147; 204/435
[58] Field of Search .............. 204/1 T, 1 C, 404, 435, 204/147, 196

[56] References Cited

U.S. PATENT DOCUMENTS

| | | | |
|---|---|---|---|
| 3,000,804 | 9/1961 | Cahoon et al. | 204/435 |
| 3,471,394 | 10/1969 | Sudrabin | 204/435 |
| 3,806,439 | 4/1974 | Light et al. | 204/435 |
| 3,810,828 | 5/1974 | Lindholm | 204/435 |
| 4,006,063 | 2/1977 | Ensanian | 204/1 T |
| 4,019,129 | 4/1977 | Grau | 204/1 T |
| 4,125,440 | 11/1978 | Markovits | 204/1 T |
| 4,155,814 | 5/1979 | Tejfalussey | 204/404 |
| 4,235,688 | 11/1980 | Sudrabin et al. | 204/435 |
| 4,273,637 | 6/1981 | MacDonald et al. | 204/435 |

OTHER PUBLICATIONS

"Corrosion of Metals and Alloys", Moscow, Mettallurgizdat, 1963, pp. 353-358, by A. I. Golubev and P. V. Strekalov.

Primary Examiner—T. Tung
Attorney, Agent, or Firm—Flynn, Thiel, Boutell & Tanis

[57] ABSTRACT

The invention relates to a half cell for use in determining potential differences in a building structure, comprising a body for containing a supersaturated electrolyte such as copper sulphate solution, the body having a part which contains the electrolyte and an absorbent part which provides a surface for contacting the structure and which provides at least part of the boundary surface of the first-mentioned part, and an electrode which extends into the electrolyte.

13 Claims, 5 Drawing Sheets

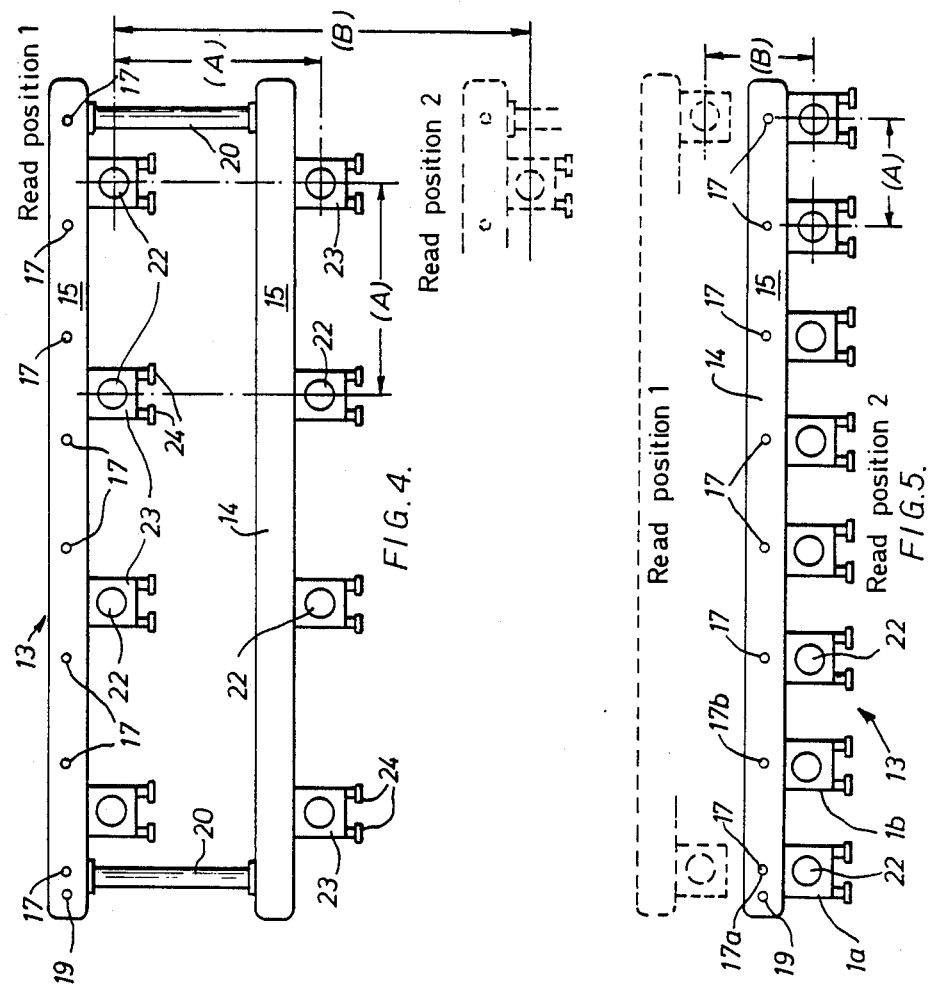

APPARATUS FOR DETERMINING POTENTIAL DIFFERENCES

The invention relates to corrosion detection, particularly that of steel in reinforced concrete structures.

Steel corrodes in concrete by an electrochemical process which involves the development of anodic, or corroding, and cathodic (passive) sites on the steel surface.

Thus regions of differing electrical potential and associated current flow patterns are established in the concrete. The effective measurement of the potentials and current densities allows a complete evaluation of the corrosionprocess occuring in the reinforcement. At present there appears to be little prospect of surveying a structure for corrosion current densities but potential can be surveyed. Hence although it can be possible to locate corroding steel in a potential survey, the rate of corrosion has not yet been quantifiable.

Potential survey methods were first used to find corrosion in buried pipelines. The method and its application to reinforced concrete was then developed for investigating corrosion in bridge decks. The general methodology of potential surveys is based on fundamental electrochemical principles, but the correlation between potential values and the risk of corrosion is empirical. It has been derived from a large number of measurements carried out on test speciments and salted bridge decks. The values, often called 'Van Deveer' criteria, have normally proved to be satisfactory for bridge decks, the structural element most frequently surveyed in developing potential (E) of a half cells used to determine that potential.

Thus:

$E < -350$ mV greater than 95% probability of corrosion $E < -200$ mV approximately 50% probability of corrosion $E < -200$ mV less than 5% probability of corrosion.

Over the years, as problems have developed in other parts of bridges and in other sturctures (e.g. buildings (houses, multi-storey offices), car parks, swimming pools, cooling towers, oil platforms, etc.), the potential survey method has been more widely used usually giving good correlation between potential value and risk of corrosion.

This is because the measurement of potential at the surface is non-destructive of the structure being surveyed. However, while potentials measured at different locations can give valuable information, such measurements do not provide a "map" or iso-potential contour lines across a structure or part thereof being surveyed. This is generally because there are no simple yet effective measuring apparatus of half cell to provide such data. (It will be understood that the half cell and the structure under survey which forms another half cell in effect, together in operation provide a "cell" or "battery", the potential or output of which can be determined).

Accordingly, it is an object of the invention to seek to provide apparatus which can overcome the disadvantages of the prior art.

According to a first aspect of the invention there is provided a half cell for use in determining potential differences in a structure, comprising a body for containing a supersaturated electrolyte, said body having a part which is for containing the electrolyte, and a part which provides a surface for contacting the structure, which part is absorbent and forms at least part of a boundary surface of the first mentioned part, and an electrode which extends into the body for immersion in the electrolyte.

According to a second aspect of the invention there is provided a half cell for use in determining potential differences in a structure, comprising a body for containing a supersaturated electrolyte, an electrode, which electrode extends into the body, and a porous plug extending into the body, terminating short of the electrode and providing a surface exteriorly of the body whereby the half cell can be contacted with a structure, for determining potential differences therein.

The porous plug may be a composite element.

The porous plug may be composite element comprising a wooden part and a sponge part, the sponge part providing said exterior surface.

The wooden part may have a part hollow interior in which the sponge part is received.

The body may be cylindrical and the porous plug may be cylindrical, of substantially the same external diameter as the body.

The body may have marker means whereby to indicate the level to which liquid for forming said supersaturated electrolyte is added to the body.

The marker means may comprise a screw thread, and said screw thread may cooperate with a screw thread of an insulated carrier of said electrode.

The carrier may have passages for an electrical connection lead of said half cell.

The wooden part may have a substantially conical nose portion directed into the body.

The electrode may be a copper electrode.

There may be a supersaturated electrolyte in said body.

The electrolyte may be copper sulphate solution.

According to a third aspect of the invention there is provided apparatus for use in determining potential differences in a structure, comprising a plurality of half cells, each half cell comprising a body for containing a supersaturated electrolyte, and electrode, which electrode extends into the body, and a porous plug extending into the body, terminating short of the electrode and providing a surface exteriorly of the body, whereby the half cell can be contacted with a structure, for determining potential differences therein, the apparatus also comprising a support, said support being adapted to hold the plurality of half cells at predetermined spacings, means electrically to connect the half cells, an electronic means for monitoring the outputs of the half cells, and means to connect the plurality of half cells with the electronic monitoring means.

The support may comprise a bar with a slide-way, a clamp for each half cell receivable in the slideway and for gripping a half cell, and an electrical socket connector comprising the means to connect the plurality of half cells with the electronic means.

There may be a further bar which is connectable in spaced, substantially parallel relating with the first mentioned bar whereby to provide a support structure for supporting the half cells in two substantially parallel rows. Each bar may be an aluminium extrusion, the slide way of each bar being directed in one direction and there being a further slideway directed in an opposite direction to the one direction, whereby the two bars may be connected together by spacer elements.

The bar may be an aluminium extrusion wherein the slide way is directed in one direction and there being a further slideway directed in an opposite direction to the one direction, whereby the two bars may be connected together by spacer elements.

The bar may be an aluminium extrusion wherein the slide way is directed in one direction and wherein there is a further slide way directed in an opposite direction to the one direction, whereby the bar may be connected with a device for moving the apparatus over a structure.

The device may comprise a wheeled frame.

The electroinc means may comprise an electronic data processor and a printer.

The electronic means may comprise an electronic data processor and a data storage means.

The data storage means may be removable, for subsequent analyses of data stored thereon.

The data storage means may alternatively be removable and include means for interfacing with a mainframe computer.

According to a fourth aspect of the invention there is provided a system for determining corrosion of a structure, comprising, a structure including an embedded corrodible element, apparatus as hereinbefore defined applied to a surface of the structure to determine potential differences and thus under surface corrosion of the element embedded in the structure.

According to a fifth aspect of the invention there is provided a method of determining the corrosion of a structure, comprising, providing a structure including an embedded corrodible element providing apparatus as hereinbefore defined, providing a supersaturated solution of an electrolyte in each of said plurality of half cells, applying said surfaces of said half cells to a surface of the structure, determining the potential differences at points under each half cell and monitoring same on said electronic monitoring means, and repeating said step at a series of other points spaced from said first points whereby to develop a plot of potential differences across the surface of the structure. Apparatus embodying the invention is hereinafter described, by way of example, with reference to the accompanying drawings, in which:

FIG. 4 shows schematically a plan view of the apparatus of FIGS. 2 and 3;

FIG. 5 shows schematically a plan view of a second embodiment of apparatus according to the invention;

Figure 1:
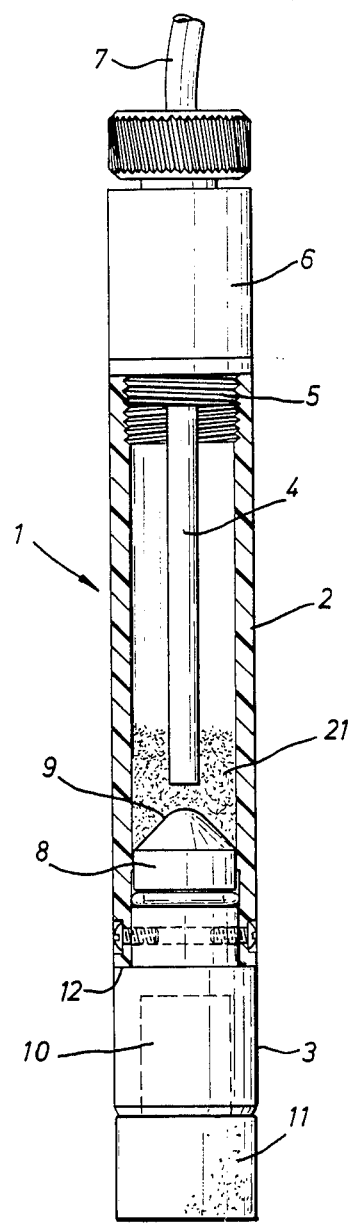
FIG. 1 is a side elevational view of a half cell according to the invention.

Referring to the drawings, the half cell 1 shown in FIG. 1, comprises a body for containing electrolyte which has a part 2 impervious to liquid and contains same, an absorbent part 3 which provides a surface for contacting a structure to be surveyed, and which forms at least part of a boundary surface of the part 2, and an electrode 4, which is copper and which terminates at a free end spaced from the part 3.

In the embodiment shown, the impervious body part 2 is a cylindrical transparent plastics tube which is threaded at one end 5 to receive a screw threaded plug 6 which carries the electrode 4, which has an electrical connection lead 7 leading therefrom. The threads also provide a marker to show the level to which the electrolyte should be filled. The porous part 3 closes the opposite end of the tube 2 and itself comprises two parts, namely a wooden plug 8 having a conical nose 9 extending towards the electrode 4, which plug 8 has a hollow extension 10 (shown by dashed lines) in which a sponge 11, usually a hard sponge is received in close-fitting engagement. The sponge 11 is removable, and when removed the extension 10 can be housed in a protective sheath such as a rubber sleeve which can be pushed over the extension 11 as far as the base (as viewed) of the tube 2.

The extension 10 has a shoulder 12 which butts against the end of the tube 2 with the nose 9 then projecting into the tube 2.

There is a seal such as 'O'-ring intermediate the length of the nose to seal against the inner surface of the tube to obviate leakage. The part 8 is secured in the tube by plastic (non-conductive) screws (not numbered) which are screwed through the wall of the tube 2 into the nose part 8.

The tube 2 and plug 3 have substantially the same external diameter as shown.

Figure 6:
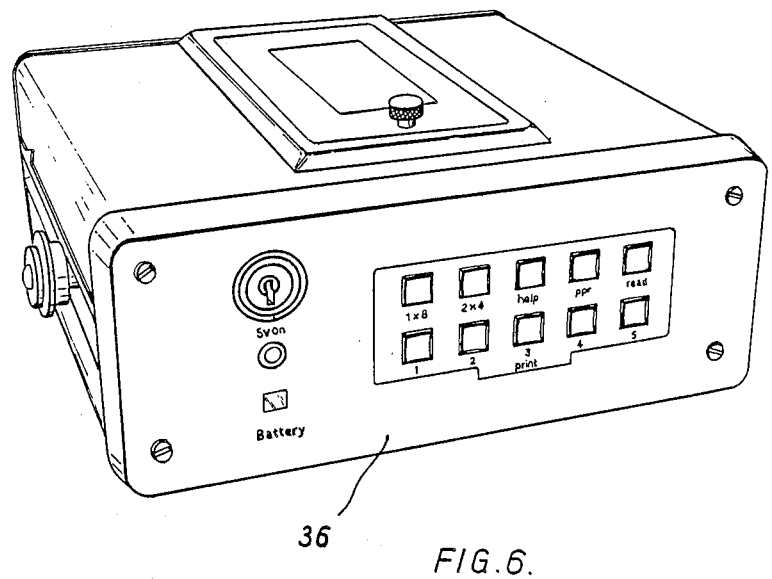
FIG. 6 shows an electronic monitor of the apparatus.

Apparatus 13 for determining potentials in a standing structure comprises a plurality of the half cells 1 of FIG. 1, a support therefore 14, electrical connection means 15 for connecting the half cells, an electronic means 36 (FIG. 6) for determining the potentials detected by the half cells and means 17 for connecting the array of half cells with the electronic means, which may include a printer.

The support 14 is an aluminium extrusion with a part of generally H-configuration 15 in cross-section, the limbs of the pair of limbs of the 'H' being angled towards each other at the free ends to provide two slide ways in one 16 of which the half cells 1 are received as shown in FIGS. 2-5. The extrusion 15 also has eight electrical sockets 17, one for each lead 7 from a respective one of eight half cells 1, the apparatus being designed to operate with eight half cells 1. The extrusion also has a 12-pin socket connector for connection with the electronic data monitoring means 36, which is battery operated. There is also an electrical connection 19 for the extrusion 15 itself.

Figure 2:
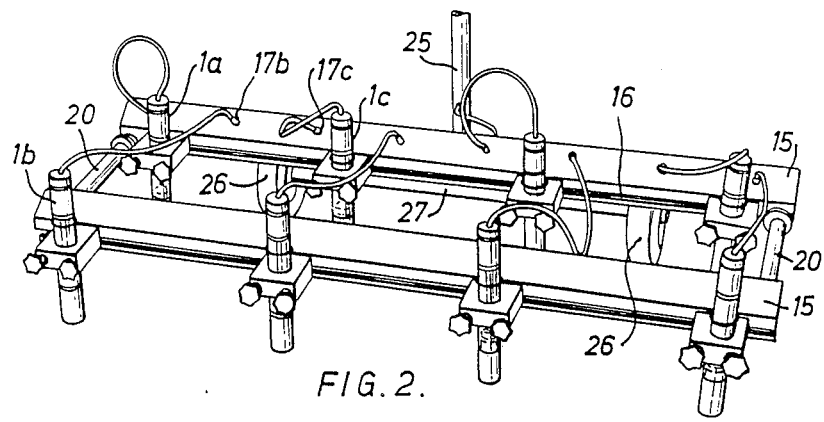
FIG. 2 is a front view of apparatus according to the invention utilising a plurality of the half cells of FIG. 1.
Figure 3:
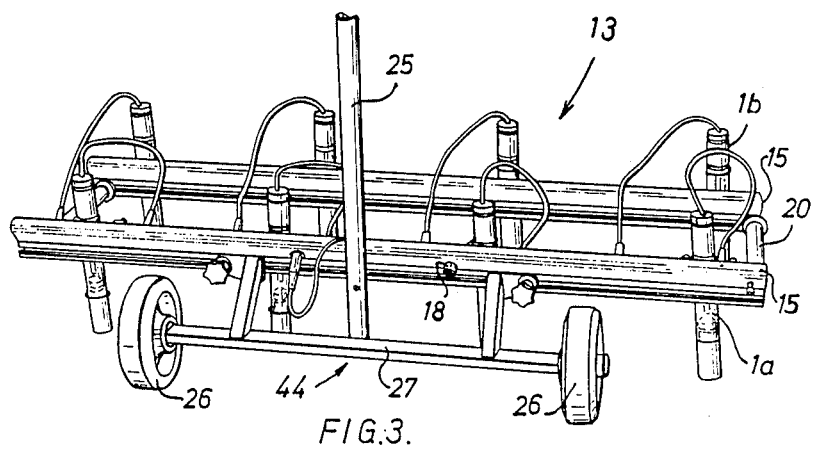
FIG. 3 is a rear view of the apparatus of FIG. 2.

The apparatus 13 may be arranged in a "parallel" kind of array of the eight half cells, as shown in FIGS. 2-4, or in an on line or series or sequential arrangement as shown in FIG. 5.

In the embodiment of FIGS. 2-4, two aluminium extrusions 15 are held in parallel arrangement by two spaced paralled spacer bars 20 which are received in facing guideways 16 of the two extrusions 15.

In operation to provide an iso-contour map of a reinforced concrete structure, eight half cells 1 are taken, each of which contains copper sulphate crystals 21. The plug or cap 6 holding the electrode is removed from each one by unscrewing, and distilled or de-ionised water poured into each one up to the level of the marker in each case (the screw thread 5), and the plastic cap 6 is replaced by screwing. The half cells 1 are each shaken well and left to stand, preferably overnight to saturate the plug 3. The cell is then topped up with water and/or copper sulphate crystals as necessary to ensure a supersaturated solution of copper sulphate electrolyte, and immediately before use the wooden plug 10 and sponge 11 are also thoroughly soaked in clean tap water.

The half cells 1 are then mounted on either two support bars 15 (FIGS. 2-4) or a single support bar (FIG. 5) by passing them through a respective hole 22 in a clamp 23 which is mounted in the slideway 16. The clamps 23 have adjustable tightening knobs 24 to secure the half cells 1 in the apertures 22 and projections which are complementary to the shape of the slideway for sliding therealong. The half cells are adjusted in position to provide equal pitches 'A', as shown in FIGS. 2-5.

In the embodiment of FIGS. 2-4, the half cells 1 are all connected by their electrical leads 7 to one support (the rear one in use), the four half cells on one support being connected to respective alternate electrical sockets, and the half cells of the other support being connected with respective alternate sockets. Thus half cell 1a is connected to socket 17a, half cell 17 is connected to socket 17b and half cell 1c is connected to socket 17c, and so on.

In the embodiment of FIG. 5, the half cells 1 are connected in series, with each half cell being connected with a respective adjacent socket, so that half cell 1a is connected with the first socket, 17a, half cell 1b is connected with the second socket 17b and so on.

Where the apparatus 13 can be applied downwardly on a structure being investigated, there may be a wheeled transport device 44 which has a handle, wheels 26, and frame 27 for slidable releasable lockable connection with a slide way opposite the slideway 16 of one extrusion 15 carrying the half cells (FIGS. 2-4) or of the extrusion 15 (FIG. 5).

The handle 25 includes a switch (not shown) and there is an electrical lead connecting the switch to the apparatus.

The electronic determining means or microprocessor 16 may be carried round the neck of the operator of the apparatus 13 by a strap. The operator in use of the apparatus to determine potentials of the structure moves the apparatus over the surface on the wheels 26 previously dampened with clean water and takes a series of readings.

In the first embodiment the apparatus is moved between positions such that each read position is spaced from the immediately preceding one by a distance "B" which is twice the pitch "A" between half cells, as shown in FIG. 4 where the second positions "Read Position 2" is shown in dashed lines.

In use of the embodiment of FIG. 5, the distance 'B' between successive read positions is equal to the pitch A.

Thus the first embodiment gives faster cover of the surface, as the distance between readings is twice as great as the in the second embodiment. The area to be covered can thus be covered in half the time, using the first embodiment.

However, the apparatus need not be used by applying downwardly to a surface. The half cells 1 can equally be applied to an overhead surface, that is vertically upwardly or to an inclined or upright surface such as a wall or leg of a bridge, oil rig or the like. In every embodiment the soaked firm sponges 11 give a firm substantially 100% contact area with the surface and allow the apparatus to remain level as they accommodate surface irrularities. The apparatus is thus orientation independent, and can be used in any attitude.

To assist an operator in a scan of a surface, he or she may lay out a grid of spacings each equal to "A" or "2A" depending on which embodiment is being used, then moves the apparatus by a grid spacing at a time to take a reading.

The potentials in the structure produce movement of ions from the potential site, through the sponge and electrolyte of the half cells 1 to provide an electrical output read by the electronic means 36.

Figure 7:
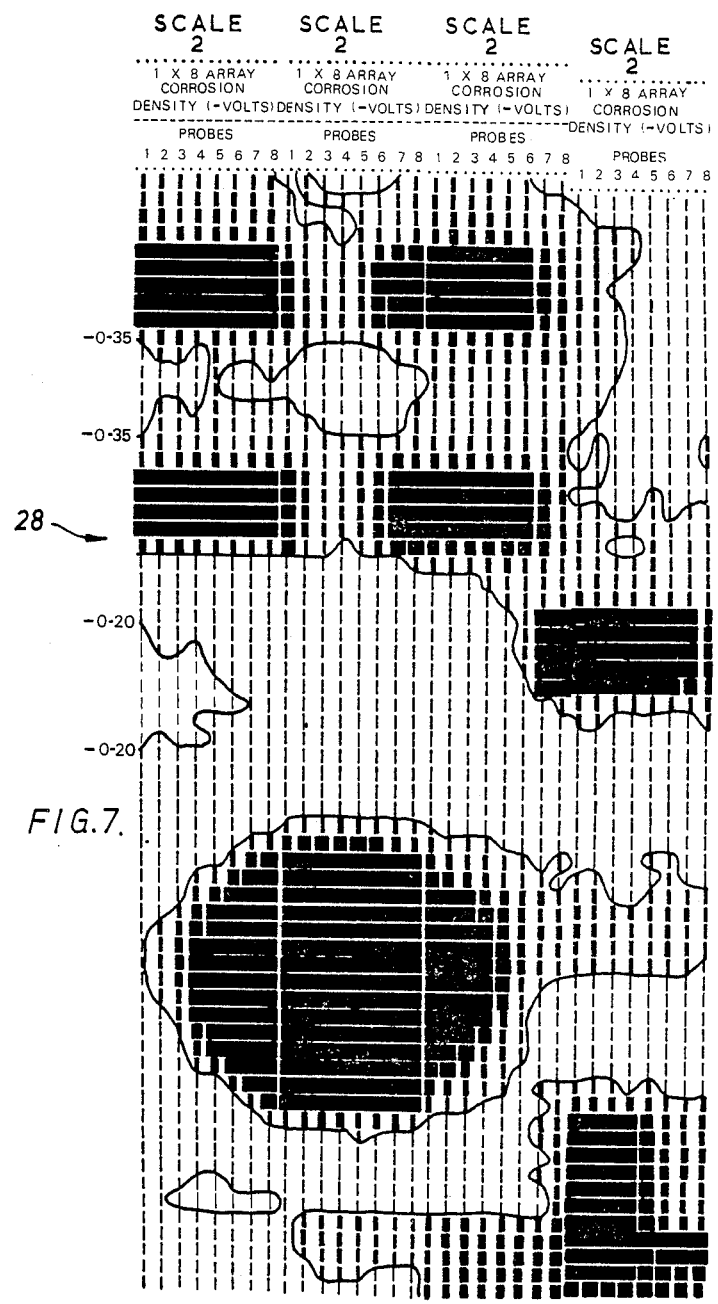
FIG. 7 shows a typical print out using the apparatus of FIG. 1.

Once a series of readings has been taken and a print out obtained the print outs can be applied, after cutting into strips, to a backing sheet, to give an iso-potential contour map like the one 28 shown in FIG. 7 the higher the negative potential values recorded the greater the probability of there being corrosion present.

Thus the multi-half-cell device of the apparatus provides a 3-dimensional analysis for the 2-dimensional area, the analyses given an indication of the intensity of density of corrosion. Stated in another way, the voltages read provide an equipotential or iso-potential contour map of the structure.

Although the microprocessor 16 has been described as being provided with a printer/or a site readings, and with a RAM whereby once it is switched off the data in its memory is lost, in an alternative the data received from each half all can be stored on an EPROM or on a battery backed-up RAM, (or any other suitable permanent form of storage) which can be processed and/or interpreted separately at a remote location such as an office removed from the structure under investigation. Thus the store may be a centronics kind of store with a parallel interface or a serial connection for connection with a mainframe computer which can process the data and provide a printed contour map of corrosion probability.

The half cell may work on the silver Calomel/Silver Chloride solution, or any other suitable system rather than the copper sulphate/copper electrode system described.

We claim:

1. Apparatus for determining potential differences in a structure, comprising:
   a pluarlity of half cells, each half cell comprising:
   (a) a body for containing a supersaturated electrolyte,
   (b) an electrode, which electrode extends into the body, and
   (c) a porous plug extending into the body and terminating short of the electrode, said porous plug being in contact with said electrolyte and providing a surface exteriorly of the body, which surfaces provides contact of said electrolyte with the structure to be monitored, for determining potential differences therein,
   a portable support device for moving the apparatus over a structure, the device comprising a frame holding the plurality of half cells at predetermined spacings from each other and wheel means separate from the half cells for shifting the device and half cells from place to place along the surface by a distance (xA) where x is a whole number and A corresponds to the spacing between adjacent half cells;
   an electronic means for successive monitoring of successive pluralities of locations on said structure by said plurality of half cells, by monitoring the outputs of the plurality of half cells; and
   means to connect the electrodes of the plurality of half cells with the electronic monitoring means.

2. Apparatus as defined in claim 1, wherein the portable frame comprises a bar with a slideway, a clamp for each half cell removably received in the slideway and gripping a half cell, and an electrical socket connector comprising the means to connect the plurality of half cells with the electronic means.

3. Apparatus as defined in claim 2, wherein the portable device includes a further bar which is connected in spaced, substantially parallel relation with the first mentioned bar, the portable device thereby supporting the half cells in two substantially parallel rows.

4. Apparatus as defined in claim 3, wherein each bar is an aluminium extrusion, wherein the slideway of each bar opens in one direction, each bar including a further slideway opening in the opposite direction, and spacer elements connecting together the two bars by engagement in opposed ones of the slideway in the two bars.

5. Apparatus as defined in claim 2, wherein the bar is an aluminium extrusion, the slideway opening in one direction, the bar including a further slideway opening in the opposite direction.

6. Apparatus as defined in claim 2, wherein the electronic means comprises an electronic data processor and a printer.

7. Apparatus as defined in claim 2, wherein the electroonic means comprises an electronic data processor and/or a data storage means.

8. Apparatus as defined in claim 7, wherein the data storage means is removable, for subsequent analyses of data stored thereon.

9. Apparatus as definied in claim 7, wherein the data storage means is removable and includes means for interfacing with a mainframe computer.

10. Apparatus as defined in claim 2, in which the half cell body is cylindrical, the clamp having a vertical hole therein through which the half cell body is vertically received, the clamps having adjustable tightening knobs to fix the half cells each at a desired height with respect to the bar.

11. A half cell as defined in claim 1, wherein the porous plug is a composite element comprising a wooden part and sponge part, the sponge part providing said exterior surface.

12. The apparatus of claim 1 in which said wheel means comprises a pair of wheels, a cross member axially spacing the wheels, which wheels rotatably support the ends of said cross member, said cross member lying parallel to and below said frame, and struts extending rigidly from said cross member up to said frame and including means securing the upper ends of said strut members to said frame, and handle means extending rigidly from said cross member and angling transversely of said cross member and frame so that said frame can be pivoted upward off the opposed structure to be monitored by pivoting said handle downwardly, said pivoting of said handle and frame being about the rotational axis of said wheels, the portable support device thus being shiftable from location to location along said structure to be monitored with the wheels rolling on said structure and the half cells spaced above and disengaged from said structure to be monitored.

13. Apparatus for determining potential differences in a structure, comprising:

a plurality of half cells, each half cell comprising:

(a) a body for containing a supersaturated electrolyte,
(b) an electrode, which electrode extends into the body, and
(c) a porous plug extending into the body, and terminating short of the electrode, said porous plug being in contact with said electrolyte and providing a surface exteriorly of the body, which surface provides contact of said electrolyte with the structure to be monitored, for determining potential differences therein, the porous plug being a composite element comprising a wooden part and a sponge part, the sponge providing said exterior surface;

a portable support device for moving the apparatus over a structure, the device comprising a frame holding the plurality of half cells at predetermined spacings from each other and wheel means separate from the half cells for shifting the device and half cells from place to place along the surface by a distance (xA) where x is a whole number and A corresponds to the spacing between adjacent half cells, said frame comprising a bar having a slideway, a clamp for each half cell received in the slideway and gripping a half cell, and an electrical socket connector, said bar being an aluminium extrusion, the slideway opening in one direction, the bar including a further slideway opening in the opposite direction, said portable support device including a further bar which is connected to and spaced in substantially parallel relation to the first mentioned bar, the portable support device therey supporting the half cells in two substantially parallel rows, the second bar also being an aluminum extrusion, and having slideways similarly situated as said first bar and spacer elements connecting together the two bars by engagement in opposed ones of the slide ways in the two bars, said wheel means comprising a pair of wheels, a cross member axially spacing the wheels, which wheels are rotatably supported on the ends of said cross member, said cross member lying parallel to and below one of said bars, and struts extending rigidly from said cross member up to said one bar and including means securing the upper ends of said strut member to said one bar at one of said slideways therein, and handle means extending rigidly from said cross member and angling transversely of said cross member and bars so that said half cells can be pivoted upward off the opposed structure to be monitored by pivoting said handle downwardly, said pivoting of said handle and bars being about the rotational axis of said wheels, said portable support device thus being shiftable from location to location along said structure to be monitored with the wheels rolling on said structure and the half cells disengaged from said structure to be monitored;

an electronic means for successive monitoring of successive pluralities of locations on said structure by said plurality of half cells, by monitoring the outputs of the plurality of half cells; and means to connect the electrodes of the plurality of half cells with the electronic means.

* * * * *